United States Patent
Gray

[11] Patent Number: 5,836,902
[45] Date of Patent: Nov. 17, 1998

[54] SPLINT

[76] Inventor: James C. Gray, 2405 Alcoa Hwy., Knoxville, Tenn. 37920

[21] Appl. No.: 759,800

[22] Filed: Dec. 3, 1996

[51] Int. Cl.[6] .................. A61F 5/00; A61F 5/37
[52] U.S. Cl. ................ 602/5; 602/20; 602/21; 128/882
[58] Field of Search .................. 602/20, 21, 22, 602/5–9, 12, 27, 62–64; 128/878, 879, 882, 877, 876

[56] References Cited

U.S. PATENT DOCUMENTS

| | | |
|---|---|---|
| 1,716,221 | 6/1929 | Fernie . |
| 1,726,728 | 9/1929 | Adams . |
| 3,117,786 | 1/1964 | Anderson . |
| 3,152,337 | 10/1964 | Barry ................................. 2/159 |
| 3,555,564 | 1/1971 | Miskell et al. ..................... 2/168 |
| 3,581,740 | 6/1971 | Sherbourne . |
| 3,605,120 | 9/1971 | Hobbs ................................ 2/159 |
| 3,779,550 | 12/1973 | Benoun et al. . |
| 3,788,307 | 1/1974 | Kistner . |
| 3,903,878 | 9/1975 | Spann . |
| 3,911,497 | 10/1975 | Lewis, Jr. et al. .................... 2/16 |
| 3,944,220 | 3/1976 | Fasano . |
| 4,041,940 | 8/1977 | Frankel et al. . |
| 4,167,044 | 9/1979 | Girard . |
| 4,173,218 | 11/1979 | Cronin . |
| 4,183,098 | 1/1980 | Knowles, Jr. ...................... 2/16 |
| 4,417,570 | 11/1983 | Finnieston . |
| 4,451,044 | 5/1984 | Elliot, Jr. . |
| 4,558,694 | 12/1985 | Barber . |
| 4,565,195 | 1/1986 | Eisenberg . |
| 4,573,456 | 3/1986 | Spann . |
| 4,675,914 | 6/1987 | Mitchell .......................... 2/161 A |
| 4,698,850 | 10/1987 | Patton, Sr. et al. ................. 2/159 |
| 4,716,892 | 1/1988 | Brunswick . |
| 4,719,906 | 1/1988 | DeProspero . |
| 4,765,319 | 8/1988 | Finnieston et al. . |
| 4,781,178 | 11/1988 | Gordon . |
| 4,787,376 | 11/1988 | Eisenberg . |
| 4,798,199 | 1/1989 | Hubbard et al. . |
| 4,807,609 | 2/1989 | Meals . |
| 4,883,073 | 11/1989 | Aziz .................................. 128/878 |
| 4,911,150 | 3/1990 | Farley . |
| 4,925,187 | 5/1990 | Fleenor et al. . |
| 4,945,925 | 8/1990 | Garcia ............................... 128/877 |
| 4,960,114 | 10/1990 | Dale . |
| 4,977,890 | 12/1990 | Mann . |
| 5,295,948 | 3/1994 | Gray ................................ 602/21 X |

Primary Examiner—Richard J. Apley
Assistant Examiner—Kim M. Lee
Attorney, Agent, or Firm—Pitts & Brittian, P.C.

[57] ABSTRACT

An improved splint for at least partially immobilizing a portion of the body of a patient and/or resistively exercising portions of a patient's body. The splint comprises a splint body fabricated of a elastomeric material, the splint body having an inner surface for closely engaging a portion of the patient's body. The splint is comprised of at least two interconnected ribs and the splint body is configured to fully surround the body portion. The splint defines a flexible span for opening the splint to the receive the body portion. The improved splint also includes a suitable securing means for securing the splint around the body of the patient.

24 Claims, 5 Drawing Sheets

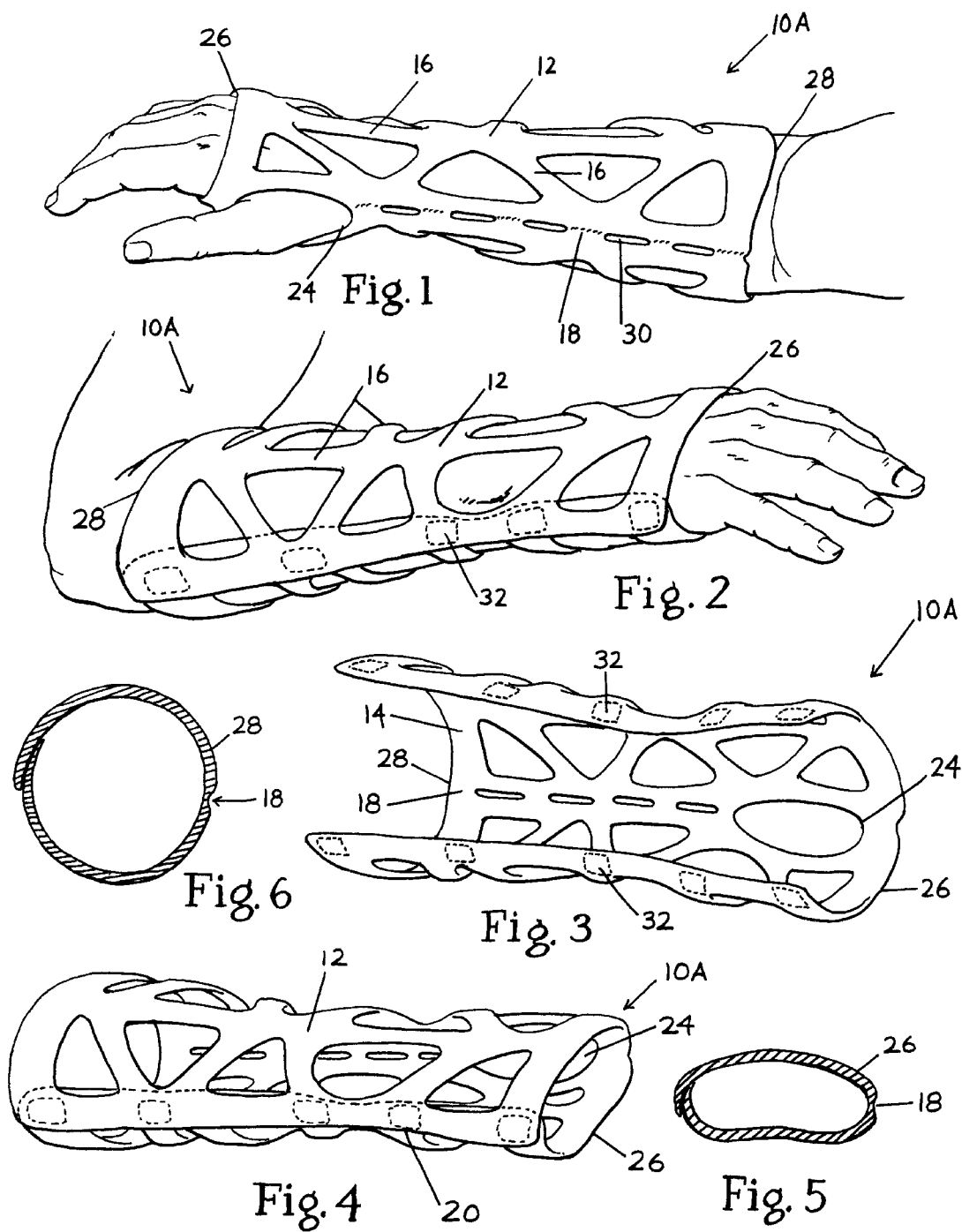

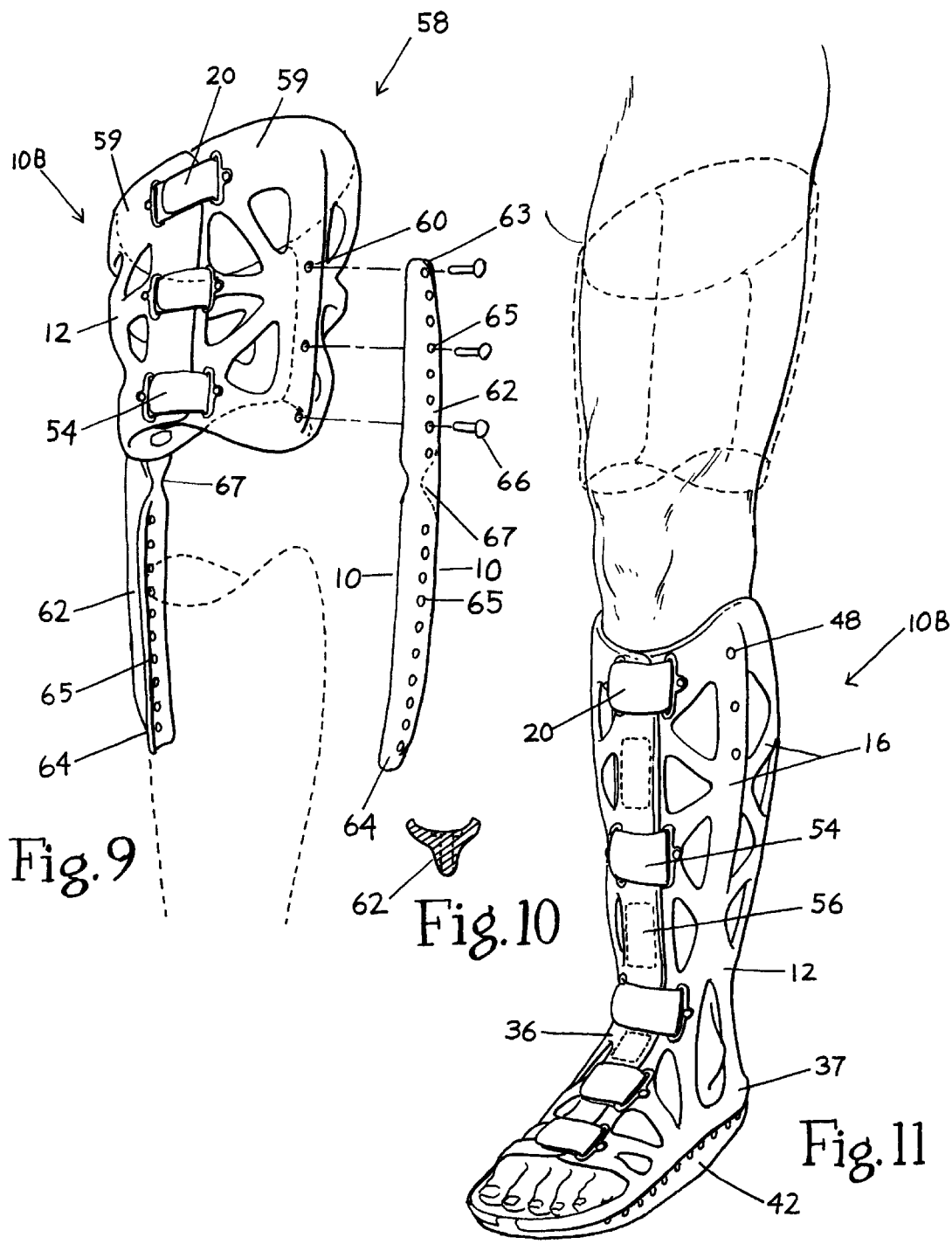

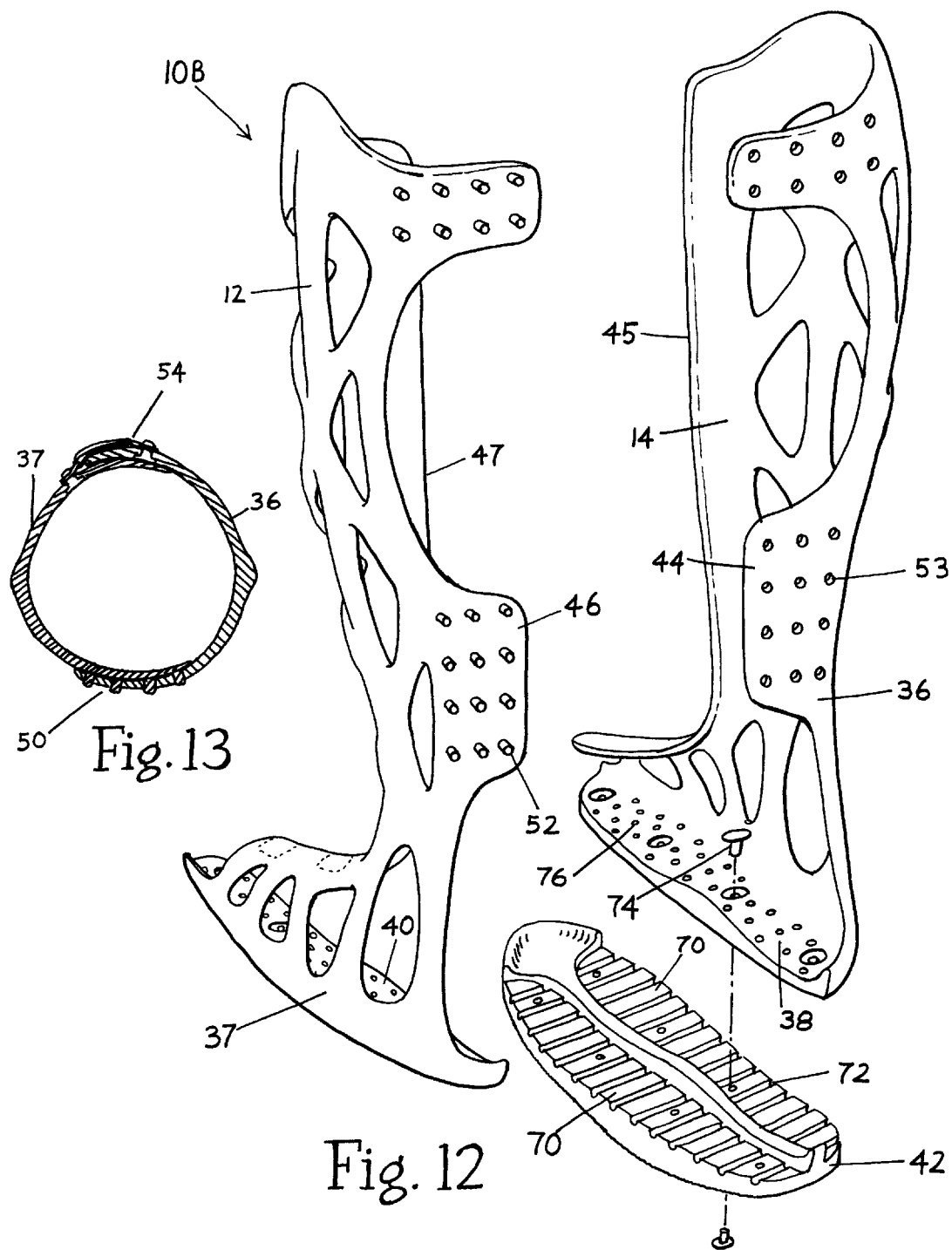

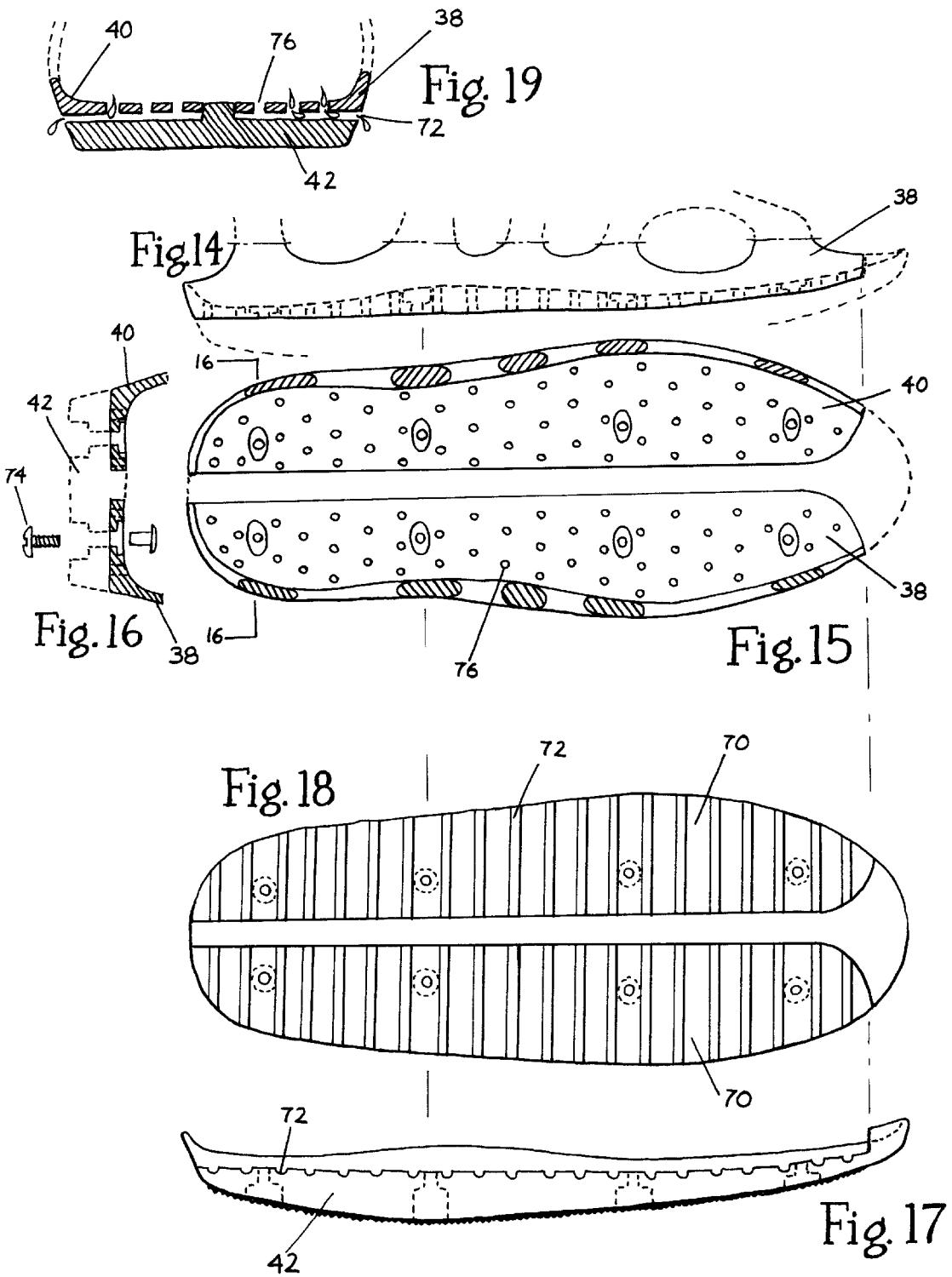

SPLINT

This application in part discloses and claims subject matter disclosed in my earlier filed pending application, Ser. No. 08/559,159, filed Nov. 13, 1995, which is a continuation-in-part of my earlier filed pending application, Ser. No. 08/178,841, filed Jan. 7, 1994, now U.S. Pat. No. 5,584,799 which issued on Dec. 17, 1996, which is a continuation-in-part application of my earlier filed application, Ser. No. 07/947,938, filed Sep. 21, 1992, which is now U.S. Pat. No. 5,295,948 and issued on Mar. 22, 1994.

TECHNICAL FIELD

This invention relates to an improved splint for at least partially immobilizing selected portions of a patient's body.

BACKGROUND ART

Splints and casts have long been used to immobilize body joints, or the ends of fractured bones. However, conventional splints and casts are generally rigid devices which are secured to the body proximate the point of an injury, and result in total immobilization of the area to which they are applied, even if total immobility is unnecessary. Attempts have been made to construct splints which do allow some residual mobility such as those disclosed in U.S. Pat. Nos. 4,719,906 issued to R. DeProspero on Jan. 19, 1988; and 4,781,178 issued to K. M. Gordon on Nov. 1, 1988.

However, such splint devices tend to be complex and provide little selectivity as to the extent of mobility allowed the portion of the body to which they are applied. Other splints and similar devices are disclosed in the following U.S. Letters Patent:

| U.S. Pat. No. | Patentee(s) | Issue Date |
|---|---|---|
| 1,716,221 | T. R. Fernie | June 4, 1929 |
| 1,726,728 | W. G. Adams | Sept. 3, 1929 |
| 3,117,786 | J. H. Anderson | Jan. 14, 1964 |
| 3,152,337 | G. D. Barry | Oct. 13, 1964 |
| 3,555,564 | E. Miskell, et al. | Jan. 19, 1971 |
| 3,581,740 | R. D. Sherbourne | June 1, 1971 |
| 3,605,120 | H. B. Hobbs | Sept. 20, 1971 |
| 3,779,550 | S. M. Benoun, et al. | Dec. 18, 1973 |
| 3,788,307 | H. M. Kistner | Jan. 29, 1974 |
| 3,903,878 | D. C. Spann | Sept. 9, 1975 |
| 3,911,497 | F. H. Lewis, Jr., et al. | Oct. 14, 1975 |
| 3,944,220 | T. Fasano | Mar. 16, 1976 |
| 4,041,940 | S. A. Frankel, et al. | Aug. 16, 1977 |
| 4,167,044 | L. E. Girard | Sept. 11, 1979 |
| 4,173,218 | P. S. Cronin | Nov. 6, 1979 |
| 4,183,098 | M. V. Knowles, Jr. | Jan. 15, 1980 |
| 4,417,570 | A. Finnieston | Nov. 29, 1983 |
| 4,451,044 | D. D. Elliot, Jr. | May 29, 1984 |
| 4,558,694 | L. M. Barber | Dec. 17, 1985 |
| 4,565,195 | J. H. Eisenberg | Jan. 21, 1986 |
| 4,573,456 | D. C. Spann | Mar. 4, 1986 |
| 4,675,914 | R. Mitchell | June 30, 1987 |
| 4,698,850 | E. E. Patton, Sr., et al. | Oct. 13, 1987 |
| 4,716,892 | S. Brunswick | Jan. 5, 1988 |
| 4,765,319 | A. Finnieston, et al. | Aug. 23, 1988 |
| 4,787,376 | J. H. Eisenberg | Nov. 29, 1988 |
| 4,798,199 | V. M. Hubbard, et al. | Jan. 17, 1989 |
| 4,807,609 | R. A. Meals | Feb. 28, 1989 |
| 4,883,073 | F. Aziz | Nov. 28, 1989 |
| 4,911,150 | M. D. Farley | Mar. 27, 1990 |
| 4,925,187 | C. R. Fleenor, et al. | May 15, 1990 |
| 4,954,925 | R. F. Garcia | Aug. 7, 1990 |
| 4,960,114 | C. L. Dale | Oct. 2, 1990 |
| 4,977,890 | D. B. Mann | Dec. 18, 1990 |

A number of these patents disclose devices to be used in particular sports in order to prevent injury. Specifically, those patents issued to Fernie ('221), Adams ('728), Anderson ('786), Barry ('337), Hobbs ('120), Benoun ('550), Lewis ('497), Knowles ('098), Elliot ('044), Eisenberg ('195 and '376), Mitchell ('914), and Fleenor ('187) are such devices. Each of these either provides for the rigid support of a portion of the body—typically the hand or foot—or provides a cushioning means for reducing the force of a blow which might otherwise cause physical damage. The Miskell ('564) patent discloses a glove for use by a surgeon, while the Garcia ('925) patent discloses a device for aiding in the placement of an intravenous tube into a patient.

Of the remaining patents which are related primarily to therapy, rehabilitation, and/or aiding the physically impaired, none discloses a device which may define varying flexibilities over the body thereof. Further, none provides for the retention of the body portion in a preselected position until force is exerted upon the device in an attempt to move the body portion. Moreover, of the casts and/or splints which are configured to surround the body portion, they are not configured to permit exposure of the body portion to air. Further, these casts can not be exposed to water and are unadjustable to accommodate swelling or the lessening of swelling. Also, the body portion surrounded by a typical cast can not be x-rayed with the cast in place.

Therefore, an object of the present invention is to provide an improved splint for at least partially immobilizing a portion of the body of a patient.

Another object of the present invention is to provide an improved splint which allows the extent of immobility imparted to be preselected, and which allows such preselected extent of immobility to be varied over the surface area covered by the splint.

A further object of the present invention is to provide an improved splint which is fabricated of an elastomeric material such that it can be trimmed to engage only that surface area of the patient's body where mobility is to be restricted.

Still another object of the present invention is to provide a splint which defines a thickness that may be selectively thinned in order to allow for greater flexibility at subsequent stages in the healing process, thereby preventing the need for purchasing several devices to accomplish complete recovery.

Yet another object of the present invention is to provide an improved splint which can also be used as a resistive exercise means.

Still a further object of the present invention is to provide an improved splint which is inexpensive to manufacture.

A further object of the present invention to provide an improved splint which is configured to be a one-piece design which surrounds a portion of a patient's body.

Further, another object of the present invention is to provide an improved splint which can be exposed to water.

It is yet another object of the present invention to provide an improved splint through which the body portion can be x-rayed.

DISCLOSURE OF THE INVENTION

Other objects and advantages will be accomplished by the present invention which provides an improved splint for at least partially immobilizing a portion of the body of a patient and/or resistively exercising portions of a patient's body. The splint comprises a splint body fabricated of a elastomeric material, the splint body having an inner surface for closely engaging a portion of the patient's body. The splint is comprised of at least two interconnected ribs and the splint body is configured to fully surround the body portion. The splint defines a flexible span for opening the splint to the receive the body portion. The improved splint also includes a suitable securing means for securing the splint around the body of the patient.

BRIEF DESCRIPTION OF THE DRAWINGS

The above-mentioned features of the present invention will become more clearly understood from the following detailed description of the invention read together with the drawings in which:

FIG. 1 is a side view of an alternate embodiment of an improved splint secured around an arm of a patient;

FIG. 2 is the opposing side view of the improved splint of FIG. 1 secured around the arm of the patient;

FIG. 3 is a perspective view of the improved splint of FIG. 1 in an open position;

FIG. 4 is a perspective view of the improved splint of FIG. 1 in a closed position;

FIG. 5 is an end view of the first end of the splint device of FIG. 1;

FIG. 6 is an end view of the second end of the splint of FIG. 1;

FIG. 9 illustrates a thigh attachment for use with the splint of FIG. 7;

FIG. 10 is a cross sectional view taken along line 10—10 of FIG. 9;

FIG. 11 is a perspective view of the splint of FIG. 7 showing the attachment holes for the thigh attachment;

FIG. 12 is an exploded view of the splint of FIG. 7;

FIG. 13 is a top view of the splint of FIG. 7;

FIG. 14 is a side view of an upper sole of the splint of FIG. 7;

FIG. 15 is a top view of the upper soles of the splint of FIG. 7;

FIG. 16 is a cross sectional view of upper soles taken along line 15—15 of FIG. 15;

FIG. 17 is a side view of the bottom sole of the splint of FIG. 7;

FIG. 18 is a top view of the bottom sole of FIG. 17; and,

FIG. 19 is a cross sectional view of the upper soles resting on the bottom sole.

BEST MODE FOR CARRYING OUT THE INVENTION

Figures 7, 8:
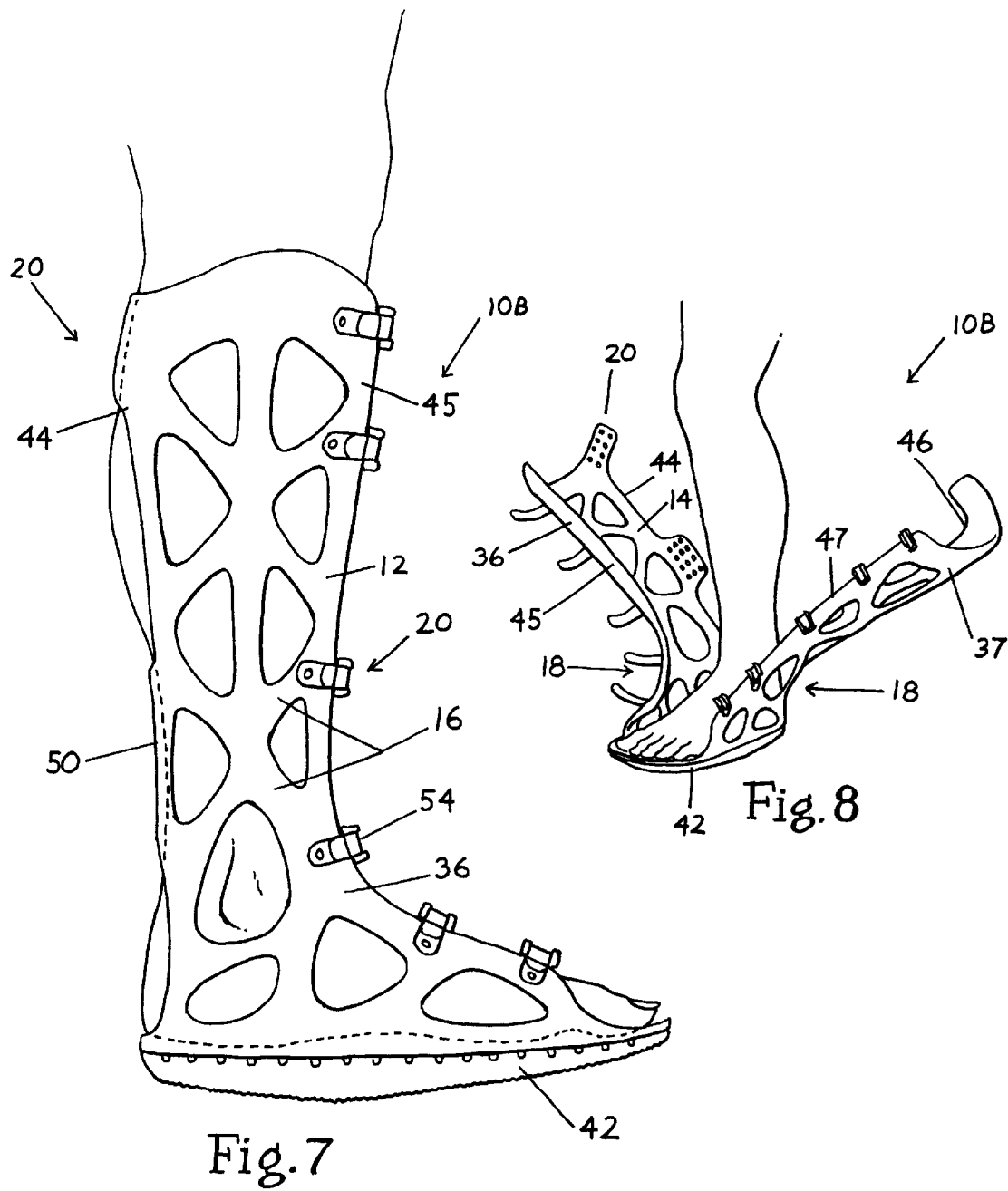
FIG. 7 is a side view of an alternate embodiment of an improved splint secured around a leg of a patient.
FIG. 8 is a perspective view of the splint of FIG. 7 in an open position.

An improved splint incorporating various features of the present invention is illustrated generally at 10 in the figures. The splint 10 of the present invention is designed to partially or totally immobilize a portion of a patient's body, and/or to provide resistive exercise for muscle or tendon therapy to that portion of the patient's body.

The splint 10 generally comprises a resilient splint body 12 which has an interior surface 14 for engaging a portion of the body of a patient. Preferably, the splint body 12 is integrally molded of an elastomeric material, such as silicone rubber, urethane, etc. Moreover, the splint body 12 is preferably molded such that the inner surface 14 is contoured to closely engage a portion of the patient's body. The splint body 12 is also molded to closely engage a portion of the patient's body as it is disposed in a desired position such that the elastomeric body 12 biases such portion of the patient's body to the desired position. This desired position may be a position which promotes proper mending of bones, or healing of tendons or muscle tissue.

It will be appreciated that the use of an elastomeric material permits the splint 10 to be worn while the wearer bathes because the material is waterproof. Further, elastomeric materials permit the passage of x-rays therethrough without interference such that the splint 10 can be worn while x-raying the body portion.

The splint 10 is specifically comprised of a plurality of interconnected ribs 16. Further, in the preferred embodiment, the splint 10 is a one-piece design configured to surround the body portion for which it is molded. The splint 10 defines a flexible span 18 integrally formed in the splint body for opening the splint 10 to receive the body portion and closing around the body portion.

Further, the splint 10 also defines a securing means 20 for securing the splint 10 in a closed position to retain it in position on the selected body portion. Such securing means 20 can include adhesive or other suitable tapes, or various releasable straps. The ribs 16 can be formed with varying thicknesses to vary the flexibility along the rib 16 and along the splint 10. Further, it will be appreciated that the use of a suitable elastomeric fabricating material which permits the splint 10 to be easily trimmed using cutting instruments generally available to a physician in general practice. Such fabrication also permits the shaving of the splint 10 in order to reduce the thickness and enhance the flexibility, which will be appreciated in the progressive states of healing. It will be noted that it may be desirable to utilize a sleeve of moisture wicking material under the splint 10 to assist in reducing edema.

The splint 10 can be formed to engage various parts of a patient's body, and to totally or partially immobilize such portions of the body of the patient. For example, FIGS. 1–6 are directed to a splint 10A configured to receive a forearm of a patient. Specifically, the splint 10A is configured to surround the forearm and wrist to at least partially immobilize the forearm and wrist of the patient. As shown in FIGS. 1 and 3, the splint 10A defines an opening 24 for receiving the thumb of the patient. In the preferred embodiment, the flexible span 18 extends along a line which bisects the thumb opening 24 and extends from the first end 26 to the second end 28 of the splint 10A, as shown in FIGS. 1 and 3. In the preferred embodiment, the flexible span 18 is defined by a line of thinned material as shown in the end views of FIGS. 5 and 6. FIGS. 5 and 6 show the end views of the first end 26 and the second end 28 of the splint 10A, respectively. Further, in the preferred embodiment, the splint 10A also defines a plurality of spaced slotted openings 30 along the flexible span 18 which ease the bending of the splint 10A and provide ventilation.

The securing means 20, as shown in FIGS. 2, 3 and 4, for securing one side of the splint 10A to the other side can be one of a variety of closures. The closures can be hook-and-loop patches 32 (as shown in the FIGS.), adjustable hook-and-loop straps or adjustable latches. It is preferable that the securing means 20 be adjustable to allow for varying sizes or for readjustment. Further, it is preferable that the splint 10A is molded in varying sizes. It will be noted from FIGS. 5 and 6 that in the preferred embodiment, the splint 10A is configured such that one side of the splint 10A can overlap the other to accommodate varying sized individuals. Further, in the case of swelling, the overlap of the sides permits the splint 10A to be readjusted when swelling goes down such that a broken or fractured arm does not have to be resplinted.

FIGS. 7–19 are directed to a splint 10B which is configured to receive a leg and foot of a patient. Specifically, the splint 10B is a molded walking splint which in the FIGS. is configured for a left leg. FIG. 7 illustrates a side view of the splint 10B which receives the leg of a patient. The splint 10B includes an inner leg portion 36 and an outer leg portion 37 and a bottom sole 42 to which each leg portion 36, 37 is secured, as shown most clearly in FIG. 12. FIG. 8 illustrates the splint 10B in an open position for receiving or removing the leg. In this embodiment, each of the leg portions 36, 37 defines a flexible span 18 at a location proximate the bottom sole 42 for opening the splint 10B to receive the leg therein.

FIGS. 7 and 8 illustrate securing means 20 which are utilized to secure the leg portions 36, 37 to one another. In the preferred embodiment, the securing means is of an adjustable overlapping configuration to stabilize the splint while it is worn by the patient. In the preferred embodiment, the rear edges 44, 46 of the inner and outer leg portions 36, 37 are secured via pin and hole locks 50 wherein the rear edge 46 of the outer leg portion 37 defines a plurality of pins 52 and the rear edge 44 of the inner leg portion 36 defines a plurality of holes 53 configured to receive the pins 52 to lock the edges 44, 46 in place. It will be noted that the pin and hole locks 50 can be replaced with heavy duty hook-and-loop fasteners.

The front edges 45, 47 of the inner and outer leg portions 36, 37 are secured together with adjustable strap fasteners 54, as shown in FIGS. 7 and 8. It will be noted that hook-and-loop straps can also be utilized. Further, when using adjustable strap fasteners 54 it may be desirable to include hook-and-loop fasteners 56 between the straps 54 for added securement, as shown in FIG. 11.

FIG. 9 illustrates a thigh attachment 58 to be utilized in conjunction with the leg splint 10B to isolate and restrict motion of the knee or immobilize a fractured leg. The thigh attachment 58 is configured to surround the thigh of the patient and in the preferred embodiment, includes two sides 59 which secure to each other in the front and the rear of the thigh. The securing means 20 illustrated in FIG. 9 includes adjustable straps 54 on the front of the attachment 58. The rear edges of the thigh attachment 58 are preferably secured in the same manner or with pins and holes. The thigh attachment 58 is secured to the leg splint 10B via two adjustable molded brackets 62 which are securable to the thigh attachment 58 and the leg splint 10B for lengthening or shortening the splint assembly Specifically, the thigh attachment 58 defines a plurality of openings 60 on opposing sides which are matable with openings 65 in the upper end 63 of each bracket 62. A self locking fastening pin 66 is inserted through each mated opening to secure the brackets 62 to the thigh attachment 58. The leg splint 10B also defines a plurality of openings 48 and the lower end 64 of each bracket 62 is secured to the leg splint 10B in the same manner.

The brackets 62 are configured to at least partially immobilize the knee. A cross sectional view of the bracket 62 is shown in FIG. 10. The brackets 62 define a hinge indentation 67 such that the brackets 62 bend at a preselected location. It will be noted that the brackets 62 can be molded to define a high degree of stiffness such that the knee can not be bent. Further, the brackets 62 can be molded at an angle to provide resistance exercise therapy.

It will be noted from the FIGS. 9, 11 and 13 (a top view of the leg splint 10B) that the thigh attachment 58 and the leg splint 10B are configured such that their respective front and rear edges overlap such that the thigh attachment 58 and the leg splint 10B can be specifically adjusted to the patient or readjusted as swelling subsides.

It will be noted that with the thigh attachment 58 being comprised of two sides 59, the opposing sides 59 of the thigh attachment 58 and the leg portions 36, 37 of the splint 10B can be detached and opened to easily remove or receive the leg of a patient.

FIG. 12 illustrates an exploded view of the leg splint 10B showing the inner and outer leg portions 36, 37 and the bottom sole 42 of the leg splint 10B. The inner leg portion 36 defines an inner upper sole 38 and the outer leg portion 37 defines an outer upper sole 40. The upper soles 38, 40 are an integrally formed portion of the respective leg portions 36, 37, as shown in FIG. 12. The bottom sole 42 defines two recesses 70 each configured to receive the inner and outer upper soles 38, 40. The upper soles 38, 40 are secured to the bottom sole 42 via self locking fasteners 74, as shown in FIG. 12. FIG. 16 illustrates a cross sectional view the upper soles 38, 40 taken along line 15—15. The bottom sole 42 is shown in phantom and illustrates how the upper soles 38, 40 and the bottom sole 42 are configured to receive the self locking fasteners 74. In the preferred embodiment, the bottom sole is fabricated from a stiffer elastomeric material.

A side view of an upper sole is shown in FIG. 14 and a top view of the inner and outer upper soles 38, 40 is shown in FIG. 15. The upper soles 38, 40 each define a plurality of lines of drain openings 76 which extend through the upper soles 38, 40. A side view of the bottom sole 42 is shown in FIG. 17 and a top view of the bottom sole 42 is shown in FIG. 18. The bottom sole 42 defines a plurality of spaced lateral grooves 72. The upper soles 38, 40 and bottom sole 42 are configured such that the lines of drain openings 76 align above the grooves 72, as shown in the cross sectional view of FIG. 19. This configuration provides ventilation and drainage for water.

It will be noted that because of the attributes of the resilient material used to manufacture the splints of the present invention, the splints can be worn and used in a variety of activities. For example, the splints can be worn while bathing or during hydrotherapy because the material is waterproof. Further, as stated above, for resilient or elastomeric materials which are not alterable by irradiation, the splints can be worn while x-rays are taken because the material does not interfere with x-rays. Moreover, the resilient and elastomeric materials can be heated to reform the splint to another desired position. Also, the splints are constructed to provide ventilation and airiness such that the skin does not become irritated and can be scratched.

It is envisioned that other embodiments may be developed beyond the embodiments discussed heretofore and the splint is not limited to the configurations set forth above. For example, a splint can be configured to surround both the upper arm and lower arm to isolate the elbow and bias the arm in a preselected position. Further, a splint can be configured to surround the hand and the fingers to at least partially immobilize the hand in a preselected position. Moreover, a splint can be configured to surround the neck to support the neck. In these embodiments, the same subject matter herein disclosed may be adapted to achieve similar results for other body portions. It is also envisioned that the embodiments can be adapted to be used on animals. It is noted that some type of deterrent against chewing the splint may be necessary when a splint is used on an animal. One possible deterrent may be impregnating the splint material with a foul tasting substance.

In light of the above, it will be recognized that the present invention provides an improved splint with great advantages over the prior art. Unlike conventional splints, the splint 10 allows the physician to preselect the extent to which the patient's body is immobilized, and a splint 10 can impart greater immobility to certain portions of the patient's body which it contacts than others. The ability to trim or otherwise control the flexibility of the splint 10 to fit the particular injury or application makes it more versatile than conventional splints and obviates the need for various different splint configurations for the same general body portion. This ability to trim or adjust the flexibility of the splint 10 also allows openings to be cut in the body 12 of the splint to provide access to lacerations without compromising the immobilization of the patient's body portion. The splint 10 can be used to immobilize, or partially immobilize, bone fractures, or damaged tendons or muscles, and can also be used as to resistively exercise muscles and/or tendons to overcome or prevent atrophy of such tissues. Moreover, the splint 10 can be used as a brace for correcting or reorienting deformities of various portions of a patient's body. For example, patients with radial nerve damage ("wrist drop") can utilize the splint to reorient the affected hand to a natural position. Similarly, the splint 10 can be used to reorient hands deformed by osteoarthritis. Further, the splint 10 can be utilized to prevent or alleviate carpal tunnel syndrome.

While a preferred embodiment has been shown and described, it will be understood that there is no intent to limit the invention to such disclosure but rather it is intended to cover all modifications and alternate constructions falling within the spirit and scope of the invention as defined in the appended claims.

I claim:

1. An improved splint for biasing a body portion of a patient to a preselected position and for at least partially immobilizing the body portion, said device comprising:

a splint body preformed to restrain the body portion in said preselected position, said splint body defining at least two ribs which are interconnected in a manner such that the body portion is biased in said preselected position, said splint body integrally fabricated of a resilient material to at least partially,immobilize the body portion, said splint body being configured to surround the body portion, said splint body defining a flexible span integrally formed in said splint body for opening the splint to receive the body portion.

2. The improved splint of claim 1 wherein said at least two ribs are interconnected in a manner such that a plurality of openings are defined each of which revealing a portion of the skin of the body portion.

3. The improved splint of claim 1 wherein each of said at least two ribs defines a preselected thickness, when in an uncompressed state, to achieve a preselected degree of flexibility, said preselected thickness varying along a length and width of each of said at least two ribs.

4. The improved splint of claim 1 wherein said resilient material defines a modulus of elasticity to achieve a preselected degree of flexibility.

5. The improved splint of claim 1 wherein said resilient material defines a softening temperature such that said splint body is remoldable to an alternate preselected position.

6. The improved splint of claim 1 wherein said resilient material is waterproof.

7. The improved splint of claim 1 wherein said resilient material permits the passage of x-rays therethrough such that said splint is wearable while the body portion is x-rayed.

8. The improved splint of claim 1 wherein said device further comprises securing means for securing said splint body around the body portion of the patient.

9. The improved splint of claim 1 wherein said splint body is configured to bias a wrist of the patient in said preselected position, said splint body defining a first end for receiving the hand of the patient, a second end for receiving the upper portion of the forearm, and a thumb opening for receiving the thumb of the patient, said flexible span being defined at a central portion of said splint body and extending from said first end to said second end.

10. The improved splint of claim 1 wherein said splint body is configured to surround the lower portion of the leg and foot of a patient.

11. The improved splint of claim 10 wherein said splint body is comprised of an inner leg portion, an outer leg portion, a bottom sole from which said inner leg portion and said outer leg portion extend, and a securing means for securing said inner leg portion to said outer leg portion, said splint body defining two flexible span, a first flexible span being defined by said inner leg portion proximate said bottom sole, a second flexible span being defined by said outer leg portion proximate said bottom sole.

12. The improved splint of claim 11 wherein said inner leg portion includes an inner upper sole integrally formed therewith, said outer leg portion including an outer upper sole integrally formed therewith, said bottom sole defining two recesses configured to receive said inner upper sole and said outer upper sole, said inner upper sole and said outer upper sole securable to said bottom sole.

13. The improved splint of claim 11 wherein said inner upper sole and said outer upper sole each defining a plurality of lines of drain openings, said bottom sole defining a plurality of spaced lateral grooves, said plurality of lines of drain openings being aligned with said plurality of spaced lateral grooves to provide ventilation and drainage.

14. An improved splint for biasing a body portion of a patient to a preselected position and for at least partially immobilizing the body portion, said device comprising:

a splint body preformed to restrain the body portion in said preselected position, said splint body defining at least two ribs which are interconnected in a manner such that the body portion is biased in said preselected position, said splint body integrally fabricated of a resilient material to at least partially immobilize the body portion, said splint body being configured to surround the body portion, said splint body defining a flexible span integrally formed in said splint. body for opening the splint to receive the body portion, said resilient material being waterproof; and, a securing means for securing said splint body around the body portion of the patient.

15. The improved splint of claim 14 wherein said at least two ribs are interconnected in a manner such that a plurality of openings are defined each of which revealing a portion of the skin of the body portion.

16. The improved splint of claim 14 wherein each of said at least two ribs defines a preselected thickness, when in an uncompressed state, to achieve a preselected degree of flexibility, said preselected thickness varying along a length and width of each of said at least two ribs.

17. The improved splint of claim 14 wherein said resilient material defines a modulus of elasticity to achieve a preselected degree of flexibility.

18. The improved splint of claim 14 wherein said resilient material defines a softening temperature such that said splint body is remoldable to an alternate preselected position.

19. The improved splint of claim 14 wherein said resilient material permits the passage of x-rays therethrough such that said splint is wearable while the body portion is x-rayed.

20. The improved splint of claim 14 wherein said splint body is configured to bias a wrist of the patient in said preselected position, said splint body defining a first end for receiving the hand of the patient, a second end for receiving the upper portion of the forearm, and a thumb opening for receiving the thumb of the patient, said flexible span being defined at a central portion of said splint body and extending from said first end to said second end.

21. The improved splint of claim 14 wherein said splint body is configured to surround the lower portion of the leg and foot of a patient.

22. The improved splint of claim 21 wherein said splint body is comprised of an inner leg portion, an outer leg portion, a bottom sole from which said inner leg portion and said outer leg portion extend, and a securing means for securing said inner leg portion to said outer leg portion, said splint body defining two flexible spans, a first flexible span being defined by said inner leg portion proximate said bottom sole, a second flexible span being defined by said outer leg portion proximate said bottom sole.

23. The improved splint of claim 22 wherein said inner leg portion includes an inner upper sole integrally formed therewith, said outer leg portion including an outer upper sole integrally formed therewith, said bottom defining two recesses configured to receive said inner upper sole and said outer upper sole, said inner upper sole and said outer upper sole securable to said bottom sole.

24. The improved splint of claim 23 wherein said inner upper sole and said outer upper sole each defining a plurality of lines of drain openings, said bottom sole defining a plurality of spaced lateral grooves, said plurality of lines of drain openings being aligned with said plurality of spaced lateral grooves to provide ventilation and drainage.

\* \* \* \* \*